(12) United States Patent
Yan et al.

(10) Patent No.: US 8,642,795 B2
(45) Date of Patent: Feb. 4, 2014

(54) PROCESS FOR PRODUCING A CONJUGATED UNSATURATED FATTY ACID

(75) Inventors: Youchun Yan, Wormerveer (NL); Shuhong Cheng, Anqing (CN); Jeroen Monster, Wormerveer (NL)

(73) Assignee: Stepan Specialty Products, LLC, Wilmington, DE (US)

( * ) Notice: Subject to any disclaimer, the term of this patent is extended or adjusted under 35 U.S.C. 154(b) by 316 days.

(21) Appl. No.: 12/960,920

(22) Filed: Dec. 6, 2010

(65) Prior Publication Data

US 2011/0301371 A1  Dec. 8, 2011

(30) Foreign Application Priority Data

Dec. 14, 2009 (CN) .......................... 2009 1 0249088
Feb. 11, 2010 (EP) ..................................... 10250232

(51) Int. Cl.
*C07C 51/347* (2006.01)

(52) U.S. Cl.
USPC ....................................... 554/126; 424/78.03

(58) Field of Classification Search
None
See application file for complete search history.

(56) References Cited

U.S. PATENT DOCUMENTS

| | | | |
|---|---|---|---|
| 2,242,230 A | 5/1941 | Burr | |
| 6,409,649 B1 * | 6/2002 | Reaney | 554/126 |
| 6,479,683 B1 | 11/2002 | Abney | |
| 7,115,759 B2 | 10/2006 | Saebo et al. | |
| 7,193,096 B2 * | 3/2007 | Yan et al. | 554/126 |
| 7,417,159 B2 * | 8/2008 | Galvez et al. | 554/126 |
| 7,910,757 B2 * | 3/2011 | Bhaggan et al. | 554/126 |
| 2007/0078274 A1 * | 4/2007 | Dianoczki et al. | 554/126 |

FOREIGN PATENT DOCUMENTS

| | | |
|---|---|---|
| EP | 799033 | 10/1997 |
| EP | 839897 | 5/1998 |
| EP | 902082 | 3/1999 |
| EP | 0902082 A1 * | 3/1999 |
| EP | 1493801 * | 1/2005 |
| WO | 97/46230 | 12/1997 |
| WO | WO 2006/082093 * | 8/2006 |

OTHER PUBLICATIONS

Moore, T., XVII. Spectroscopic changes in fatty acaids, 1937, Biochemical Journal, vol. 1, part. 1, pp. 138-154.*
Moore, "Spectroscopic changes in fatty acids", *Biochemical Journal*, 31: 138-154 (1937).
Sastry et al., "Isomerised Safflower Oil", *Paint Manufacture*, 40(8): 32-34 (1970).

* cited by examiner

*Primary Examiner* — Yate K Cutliff
(74) *Attorney, Agent, or Firm* — Barnes & Thornburg LLP; Brian R. Dorn

(57) ABSTRACT

A process for producing a conjugated di- or poly-unsaturated fatty acid having from 12 to 24 carbon atoms, or a salt or ester thereof, comprises: reacting a non-conjugated free fatty acid, or a salt or ester thereof, with a base in the presence of an alcoholic solvent comprising ethanol; and separating the conjugated fatty acid from the reaction mixture, wherein the separation of the conjugated fatty acid from the reaction mixture comprises contacting the reaction mixture with an aqueous salt solution and removing a liquid phase which comprises the salt solution and at least a part of the solvent from a solid phase which comprises a salt of the conjugated fatty acid.

14 Claims, No Drawings

PROCESS FOR PRODUCING A CONJUGATED UNSATURATED FATTY ACID

RELATED APPLICATIONS

This application claims priority under 35 U.S.C. §119 or 365 to Chinese Patent Application No. 200910249088.X, filed Dec. 14, 2009 and to European Patent Application No. EP 10250232.5, filed Feb. 11, 2010. The entire teachings of the above applications are incorporated herein by reference.

This invention relates to a process for producing a conjugated di- or poly-unsaturated fatty acid having from 12 to 24 carbon atoms, or a salt or ester thereof.

Conjugated isomers of long chain polyunsaturated fatty acids are known to have potential benefits, for example when used in food products. Examples of such acids include the isomers of conjugated linoleic acid (CLA); typically, the cis 9, trans 11 and trans 10, cis 12 isomers are the most abundantly present isomers in CLA, and they are generally present in a 1:1 weight ratio when synthesised chemically. Conjugated isomers can be produced from the corresponding non-conjugated fatty acids, usually by isomerisation in the presence of a base.

EP-A-0799033 discloses a process for producing conjugated isomers in which ethylene glycol is used. Ethylene glycol however has the disadvantage that it is very difficult to remove completely from the reaction product of the isomerisation process. Moreover, the yields of desired conjugated polyunsaturated isomers in the reaction product of the conversion in the presence of base are relatively low.

According to WO 97/46230, conjugated linoleic acids can be obtained by isomerisation of linoleic acid or safflower oil by subjecting the starting material to base (KOH) in propylene glycol at 180° C. The reaction product contains relatively large amounts of isomers other than the desired conjugated linoleic isomers. This may be due to the severe reaction conditions. EP-A-0839897 also describes a process for producing conjugated linoleic acids by subjecting fats containing linoleic acid to base in propylene glycol.

EP-A-0902082 discloses a process for the preparation of materials comprising mainly conjugated isomers of long chain polyunsaturated fatty acids wherein an oil or a free fatty acid composition or an alkyl ester composition thereof, containing at least 25 wt % of at least one isomer other than the conjugated isomers of long chain polyunsaturated fatty acids, is subjected to a treatment with a base in a solvent and wherein the solvent is an alcohol with at least 3 C-atoms and at least two hydroxy groups having: a ratio of number of C-atoms: number of OH groups of at least 1.25 but less than 3.5, preferably from 1.5 to 2.75, while the reaction is carried out between 100 and 180° C., more preferably between 120 and 180° C.

U.S. Pat. No. 2,242,230 discloses a process for producing conjugation in unconjugated polyenes. The process is carried out under non-aqueous conditions and any water that is formed in the process is removed from the reaction. The process is carried out in the presence of a base which is an alcoholic solution of dry KOH in dry alcohol or a solution of an alkali metal alkoxide in alcohol formed by reaction of the alkali metal with the alcohol. The presence of water is avoided, since the document teaches that water inhibits the reaction and reduces the yield.

Sastry et al, "Isomerised Safflower Oil", Paint Manufacture, vol 40, no 8, 1 Aug. 1970, pages 32 to 34 describes the isomerisation of safflower oil followed by elaidinisation to obtain trans, trans isomers. The reaction is carried out at 210-215° C. and substantial amounts of trans, trans isomers are obtained during the first isomerisation step.

Moore, "Spectroscopic changes in fatty acids", Biochemical Journal, vol 31, 1937, pages 138-154 relates to the changes in UV absorption spectra of fats treated with sodium hydroxide. Following saponification, the fats are refluxed for 24 hours.

U.S. Pat. No. 6,479,683 discloses a process for producing conjugated fatty acid esters by the reaction of an ester with an alkali metal alkoxide catalyst in a monohydric alcohol. It is evident from the materials used that the process is carried out in the absence of water.

EP-A-1493801 discloses a process for producing a conjugated di- or poly-unsaturated fatty acid having from 12 to 24 carbon atoms, or a salt or ester thereof, which comprises reacting a non-conjugated free fatty acid, or a salt or ester thereof, with a base in the presence of a solvent comprising a monohydric alcohol having from 1 to 6 carbon atoms, wherein the reaction is carried out at a temperature of from 120° C. to 200° C. in the presence of water in an amount of at least 4% by weight based on alcohol.

It has been found that processes using ethanol and water of the type described in EP-A-1493801, when carried out on a large scale, can have the disadvantage that the product can contain significant amounts of ethyl esters of the conjugated fatty acid. Although the ethyl esters are present in a relatively small amount (typically 1.5 to 2.5% by weight of the product), they can be very difficult to remove and so the overall purity of the product is reduced to undesirable levels.

U.S. Pat. No. 7,115,759 relates to the manufacture of CLA using alcoholate catalysts. Residual alcohol is stated as being removed either by mild acid wash (e.g., with citric acid) or by rapid separation of the phases after acidifying with strong acid We have now found a process for producing conjugated di- or poly-unsaturated fatty acids having from 12 to 24 carbon atoms, or salts or esters thereof, which employs an alcoholic solvent (such as a mixture of ethanol and water) but which ameliorates the disadvantages of the process described above by allowing the formation of a product that has a lower content of esters. Therefore, the final product can be made more pure.

Accordingly, the invention provides a process for producing a conjugated di- or poly-unsaturated fatty acid having from 12 to 24 carbon atoms, or a salt or ester thereof, which comprises: reacting a non-conjugated free fatty acid, or a salt or ester thereof, with a base in the presence of an alcoholic solvent; and separating the conjugated fatty acid from the reaction mixture, wherein the separation of the conjugated fatty acid from the reaction mixture comprises contacting the reaction mixture with an aqueous salt solution and removing a liquid phase which comprises the salt solution and at least a part of the solvent from a solid phase which comprises a salt of the conjugated fatty acid.

The invention is at least partly based on the finding that the formation of esters between the fatty acid and the solvent is a problem when the process is carried out on a large scale, the insight that the problem occurs during the separation of the fatty acid product from the reaction mixture as a result of the presence of solvent and acid at that stage and the unexpected finding that the addition of a salt solution causes the solvent to separate more effectively from the solids comprising the conjugated free fatty acid as its salt.

Conjugated fatty acids are di- or poly-unsaturated i.e., they contain at least two carbon-carbon double bonds. Typically, the fatty acids contain 2, 3, 4 or 5 carbon-carbon double bonds, preferably two carbon-carbon double bonds. The carbon-carbon double bonds are conjugated with each other (i.e., they are spaced from each other in the molecule by one carbon-carbon single bond). The starting materials that are used in the process comprise the corresponding non-conjugated fatty acids i.e., the carbon-carbon double bonds are separated from each other in the molecule by more than a single carbon-carbon bond and they are preferably separated from each other by one methylene group.

The term fatty acid and related terms used herein refers to carboxylic acids comprising an alkyl or alkenyl group (comprising two or more carbon-carbon double bonds) which may be branched or straight chain, but is preferably straight chain. The carboxylic acid contains from 12 to 24 carbon atoms, preferably from 14 to 22 carbon atoms, more preferably from 16 to 20 carbon atoms and most preferably 18 carbon atoms, including the carbon atom of the carboxylic acid group. The non-conjugated fatty acid and the conjugated fatty acid are preferably C18:2 fatty acids, more preferably they are linoleic acid and conjugated linoleic acid (CLA). The fatty acids can be mixtures of two or more fatty acids or isomers thereof.

The fatty acid that is produced in the process of the invention may be a free fatty acid, or a salt or ester thereof, or a mixture of two or more of these materials. Salts include salts with alkali metals and alkaline earth metals such as sodium, potassium, calcium and magnesium, preferably sodium or potassium. Esters include mono-, di- and tri-glycerides and mixtures thereof, and $C_1$ to $C_6$ alkyl esters (where the alkyl group can be straight chain or branched). Typically, salts and free acids are produced in the process. Salts can be converted to free acids by raising the pH of the reaction mixture at the end of the process. Free acids can be converted to esters by esterification reactions that are well-known in the art.

The non-conjugated free fatty acid, or salt or ester thereof, that is used as the starting material for the process, is preferably selected from the group consisting of vegetable oils, free acids derived from these oils and $C_1$ to $C_6$ alkyl esters of these free acids (where the alkyl group can be straight chain or branched). The non-conjugated fatty acid, or salt or ester thereof, may be present in the starting material in an amount of from 10 to 100% by weight, more preferably from 25% to 100% by weight, such as from 25% to 90% by weight. Preferred starting materials are vegetable oils, and it is more preferred that the vegetable oil is selected from sunflower oil, rape seed oil, soy bean oil, safflower oil, linseed oil and mixtures thereof. Safflower oil is a particularly preferred vegetable oil.

The alcoholic solvent that is used in the of the invention preferably comprises a monohydric alcohol having from 1 to 6 carbon atoms, or mixtures thereof, and more preferably comprises ethanol. Preferably, the solvent further comprises water in an amount of at least 4% by weight based on alcohol. Other co-solvents may be present in amounts up to 50% by weight based on alcohol, preferably up to 40%, more preferably up to 30%, such as up to 20% or up to 10% by weight based on alcohol. However, preferably the solvent comprises substantially no co-solvents other than alcohol and water or comprises said other co-solvents in an amount of less than 5%, more preferably less than 2%, even more preferably less than 1% such as less than 0.1% by weight based on alcohol. Preferably, the amount of water is from 5% to 35% by weight based on alcohol. The content of water refers to the total water content and includes water present in the starting materials as well as any added water. Water may be derived from water added to the system and/or may be already present in the alcohol solvent or the other starting materials in the process, including the base and the fatty acid. Therefore, depending on the water content of the starting materials, it may or may not be necessary to add water to the system. The amount of water in the process of the invention can be determined by methods well-known in the art, by analysis of the starting materials and/or the reaction mixture. A suitable example of a method for determining water content is the Karl Fischer method.

The reaction is preferably carried out as described in EP-A-1493801, the contents of which are incorporated herein by reference.

The reaction is carried out in the presence of a base. The base raises the pH of the reaction mixture. The base is suitably, for example, an alkali metal hydroxide selected from potassium hydroxide, sodium hydroxide and mixtures thereof. The molar ratio of base to non-conjugated free fatty acid, or salt or ester thereof, that is employed in the process is preferably in the range of from 2:1 to 15:1.

The process conditions for carrying out the reaction can be varied depending on the desired rate and yield of the product. The reaction is typically carried out at a temperature above the normal boiling point of the alcohol (i.e., the boiling point at atmospheric pressure), although lower temperatures can be employed. Generally, the higher the temperature of the reaction, the faster is the rate at which the reaction proceeds. The reaction is carried out at a temperature of from 120° C. to 200° C., preferably from 140° C. to 160° C. When the reaction is carried out at a temperature above the boiling point of the alcohol, the reaction is carried out at a pressure above atmospheric pressure in a vessel that can withstand pressures greater than atmospheric pressure.

The reaction is preferably carried out for a time and at a temperature to form a product comprising more than 60% by weight, more preferably more than 70% by weight, based on total fatty acid and salt and esters thereof, of cis-9, trans-11 and trans-10, cis-12 isomers of the conjugated fatty acid.

The reaction can be carried out for a time and at a temperature to form a product comprising less than 3% by weight of linoleic acid and salts and esters thereof, based on total fatty acid and salts and esters thereof.

Preferably, the reaction produces trans, trans isomers of conjugated fatty acids in an amount of less than 5%, more preferably less than 3%, even more preferably less than 1%, said percentages being by weight based on total fatty acid and salt and esters thereof. Thus, the amount of trans, trans isomers in the conjugated fatty acid which is the product of the process is preferably less than 5%, more preferably less than 3%, even more preferably less than 1%, said percentages being by weight based on total fatty acid and salt and esters thereof.

In the process of the invention, an aqueous salt solution is contacted with the reaction mixture after the reaction has been carried out.

The aqueous salt solution may comprise other solvents, such as ethanol, in addition to water. Preferably, the salt solution comprises at least 50% by weight of water based on the weight of the solvents present, more preferably at least 75% by weight, such as at least 90% by weight based on the weight of the solvents present. Most preferably, the salt solution comprises water as the only solvent.

Although the step of contacting the reaction mixture with an aqueous salt solution typically involves mixing the reaction mixture with a solution of the salt, it will be appreciated that the process may alternatively involve contacting the reaction mixture with the salt in solid form if the salt is sufficiently soluble in water present in the alcoholic solvent and if the amount of water in the solvent is sufficient to dissolve the salt.

The salt solution aids in removing the ethanol from the product conjugated fatty acid salt. The salt solution allows an increased amount of alcohol from the solvent to be removed when the liquid phase is separated from the solid phase that comprises the product fatty acid salt.

The reaction mixture comprises organic material that includes the salt of the conjugated fatty acid. The salt of the fatty acid is formed as a result of the presence of the base in the reaction mixture. Without wishing to be bound by theory, it is believed that in the conventional process the organic phase traps some of the alcohol of the solvent preventing it from passing into the aqueous phase. The addition of salt appears to aid in the release of the alcohol from the organic phase and this reduces the possibility of ester formation.

The salt solution is preferably added to the acidified reaction mixture and then the resulting mixture (i.e., of the salt solution and the reaction mixture) is preferably stirred or otherwise mixed.

The salt may be a single salt or a mixture of two or more salts.

Preferably, the salt has a solubility in water of at least 1 g per 100 ml, more preferably at least 10 g per 100 ml, at 25° C. The salt may be saturated or unsaturated in the solution.

Preferred salts are inorganic. The precise nature of the salt is not thought to be critical. Most preferred are inorganic salts that are non-toxic and are readily available at low cost. For example, preferred salts include alkali metal salts or alkaline earth metal salts of a halide, sulphate, nitrate or phosphate.

Examples of suitable salts are sodium chloride, potassium chloride, magnesium chloride, calcium chloride, sodium sulphate, potassium sulphate, magnesium sulphate, sodium nitrate, potassium nitrate, magnesium nitrate, calcium nitrate, sodium phosphate, potassium phosphate (which phosphates can be mono, di or tribasic) and mixtures thereof.

The most preferred salt is sodium chloride.

Therefore, in a preferred embodiment, the invention provides a process for producing conjugated linoleic acid (CLA), or a salt or ester thereof, which comprises: reacting a C18:2 non-conjugated free fatty acid, or a salt or ester thereof, with a base in the presence of a solvent comprising ethanol; and separating the CLA from the reaction mixture, wherein the separation of the CLA from the reaction mixture comprises contacting the reaction mixture with an aqueous sodium chloride solution and removing a liquid phase which comprises the sodium chloride solution and at least a part of the ethanol from a solid phase which comprises a salt of the CLA.

The separation steps of the process of the invention are preferably carried out at ambient pressure and at a temperature of from 20° C. to 90° C.

Optionally, the separation process comprises the removal of part of the solvent from the reaction mixture, for example by evaporation, prior to contacting with the salt solution.

The removal of the liquid phase from the solid phase preferably involves simply separating the lower aqueous layer from the solids and this may be achieved by known methods such as, for example, decanting or filtration.

The solid phase which comprises the salt of the conjugated fatty acid is preferably acidified to form free conjugated fatty acid. Acidification can be carried out using inorganic acids, such as aqueous sulphuric acid. The free fatty acid is then separated from the aqueous phase, and optionally washed and dried. The free fatty acid may optionally be further purified, for example by distillation.

The process of the invention optionally comprises one or more further steps, such as forming a mono-, di-, or tri-glyceride of the conjugated fatty acid.

The process of the invention can be carried out batchwise or as a continuous process. The process is suitable for use on a large scale in a suitable apparatus i.e., capable of the production of conjugated fatty acids or salts or esters thereof in an amount of over 50 kg, more preferably over 100 kg, per day. When the process is carried out batchwise, it is preferably carried out for a time of from 1 to 10 hours, preferably 2 to 6 hours.

It is a particular advantage of the process of the invention that it may be carried out on a relatively large scale whilst producing low amounts of esters of the conjugated fatty acid. The plural term "esters" is used to reflect the fact that different isomers of the conjugated fatty acid will generally be present and, therefore, the product will contain different ester compounds. Typically, the product contains said esters, preferably ethyl esters, in an amount of from 0.01% to 2% by weight, more preferably 0.2% to 1.2% by weight, such as from 0.6% to 1.0% by weight, based on total fatty acid and salt and esters thereof. The determination of the level of esters in the product can be carried out by methods known to those skilled in the art.

The product of the process preferably contains relatively low amounts of dialkyl ketones (DAKs). Preferably, the product contains dialkyl ketones in an amount of less than 100 ppm, more preferably less than 50 ppm, even more preferably less than 25 ppm. The dialkyl ketones are typically of the formula RR'CO, wherein R and R' are the same or different and are either saturated alkyl groups or unsaturated alkenyl groups having at least one carbon-carbon double bond (preferably one or two double bonds), the alkyl and alkenyl groups containing 12 to 24 (e.g., 12 to 20), preferably 14 to 18 carbon atoms, and being branched or straight chain, preferably straight chain. The products of the invention are preferably suitable for use in an edible product, more preferably they are suitable for use in a food product, a food supplement or a pharmaceutical product.

The products of the invention can be used as such. Alternatively, the products of the invention can be used as the starting materials for a further modification, such as enrichment in an isomer, such as the cis 9, trans 11 or the trans 10, cis 12 isomer of conjugated linoleic acid. For example, the product may be used as the staring material for a process for enriching a mixture containing different conjugated isomers of the same long chain polyunsaturated fatty acid in one of the isomers, as described in WO 97/18320, the contents of which are incorporated herein by reference.

The products of the process may be used in a food product, food supplement or pharmaceutical product. The products of the invention are optionally used as a blend with a complementary fat. For example, the blend may comprise 0.3-95 wt %, preferably 2-80 wt %, most preferably 5-40 wt % of the product of the invention and 99.7-5 wt %, preferably 98-20 wt %, most preferably 95-60 wt % of a complementary fat selected from: cocoa butter, cocoa butter equivalents, palm oil or fractions thereof, palmkernel oil or fractions thereof, interesterified mixtures of said fats or fractions thereof, or liquid oils, selected from: sunflower oil, high oleic sunflower oil, soybean oil, rapeseed oil, cottonseed oil, fish oil, safflower oil, high oleic safflower oil, maize oil and MCT-oils. Food products (which term includes animal feed) contain a fat phase, wherein the fat phase contains the product of the invention. The food products are suitably selected from the group consisting of: spreads, margarines, creams, dressings, mayonnaises, ice-creams, bakery products, infant food, chocolate, confectionery, sauces, coatings, cheese and soups. Food supplements or pharmaceutical products may be in the form of capsules or other forms, suitable for enteral or parenteral application and comprise a product of the invention.

The process of the invention will now be described with reference to the following non-limiting examples. In the examples and throughout this specification, all percentages, parts and ratios are by weight unless indicated otherwise.

EXAMPLES

Example 1

A 1000 liter jacketed pressure vessel was fitted with a mechanical stirrer and provided with a connector for nitrogen. The temperature of the vessel was controlled by injecting steam or cold water in the jacket.

The materials that were used in the process were safflower oil (300 kg), base (sodium hydroxide pellets; 110 kg) and as solvent: a mixture of ethanol (280 kg) and water (20 kg).

The conjugation of the safflower oil was carried out as follows. 300 kg safflower oil was placed in the reaction vessel. 110 kg of hydroxide pellets, dissolved in the 300 kg of solvent, was added to the reaction vessel and the obtained mixture was heated to 150° C. while stirring under nitrogen. The reaction was allowed to continue for 3 hours. The mixture was cooled to 120° C. in the pressure vessel and was transferred into another vessel for removal of the ethanol.

100 kg of a saturated solution of sodium chloride in water was added to the mixture followed by stirring for 15 minutes. The layers were then allowed to separate for 30 minutes. The bottom layer was decanted.

The top layer mixture was placed into a 10% sulfuric acid solution, the bottom layer was discarded and the top layer was washed with hot water until pH 7 was reached. The washed layer was finally dried at 80° C. for 1 hour, stored under nitrogen and submitted for analysis. The final mixture was purified further by distillation.

The product was analysed for fatty acid methyl ester (FAME), fatty acids ethyl esters and diakylketones.

Example 2 (Comparative Example)

Example 1 was repeated without the step of adding the saturated solution of sodium chloride.

Results

The analytical results were as follows:

| | Example | |
|---|---|---|
| | Example 1 | Example 2 (comparative) |
| FFA (%) | 98 | 97 |
| FA methyl ester (%) | 0 | 0 |
| FA ethyl ester (%) | 0.8 | 1.69 |
| DAK (ppm) | 0 | 0 |
| C14:0 CLA | 0.1 | 0.1 |
| C16:0 CLA | 6.8 | 6.8 |
| C16:1C CLA | 0.1 | 0.1 |
| C18:0 CLA | 2.5 | 2.5 |
| CLA TT CLA | 0.8 | 1.0 |
| CL911C CLA | 0.9 | 0.9 |
| CL1012 CLA | 0.8 | 0.8 |
| CL1113 CLA | 0.4 | 0.1 |
| C18:1C CLA | 12.4 | 12.4 |
| CLA OX CLA | 0.2 | 0.2 |
| C18:2T CLA | 0.6 | 0.5 |
| C18:2C CLA | 0.6 | 0.7 |
| C20:0 CLA | 0.3 | 0.3 |
| C20:1C CLA | 0.2 | 0.2 |
| C22:0 CLA | 0.2 | 0.2 |
| SAFA CLA | 10.0 | 10.0 |
| CT.ISO CLA | 73.0 | 73.1 |
| 911CT CLA | 36.4 | 36.4 |
| 1012TC CLA | 36.6 | 36.7 |
| TCLA CLA | 76.1 | 76.0 |
| Others CLA | 0.1 | 0.13 |

The process of the invention achieved a substantial reduction in ethyl esters compared to the process of the prior art.

The invention claimed is:

1. A process for producing a conjugated di- or poly-unsaturated fatty acid having from 12 to 24 carbon atoms, or a salt or ester thereof, which comprises:
   reacting a non-conjugated free fatty acid, or a salt or ester thereof, with a base in the presence of an alcoholic solvent comprising ethanol; and
   separating the conjugated fatty acid from the reaction mixture, wherein the separation of the conjugated fatty acid from the reaction mixture comprises
   contacting the reaction mixture with an aqueous salt solution and
   removing a liquid phase which comprises the salt solution and at least a part of the solvent from a solid phase which comprises a salt of the conjugated fatty acid.

2. The process as claimed in claim 1, wherein the salt in the aqueous salt solution has a solubility in water of at least 1 g per 100 ml at 25° C.

3. The process as claimed in claim 1, wherein the salt in the aqueous salt solution is inorganic.

4. The process as claimed in claim 3, wherein the salt in the aqueous salt solution is an alkali metal or alkaline earth metal salt of a halide, sulphate, nitrate or phosphate.

5. The process as claimed in claim 4, wherein the salt in the aqueous salt solution is sodium chloride.

6. The process as claimed in claim 1, wherein the aqueous salt solution is saturated.

7. The process as claimed in claim 1, wherein the reaction is carried out at a temperature of from 120° C. to 200° C.

8. The process as claimed in claim 1, wherein the reaction is carried out in the presence of water in an amount of at least 4% by weight based on alcohol.

9. The process as claimed in claim 1, wherein the non-conjugated fatty acid and the conjugated fatty acid are C18:2 fatty acids.

10. The process as claimed in claim 1, which further comprises acidifying the salt of the conjugated fatty acid to form free fatty acid.

11. The process as claimed in claim 10, which further comprises the step of purifying the salt of the conjugated fatty acid.

12. The process as claimed in claim 10, which further comprises the step of forming a mono-, di-, or tri-glyceride of the conjugated fatty acid.

13. The process as claimed in claim 1, wherein the non-conjugated free fatty acid, or salt or ester thereof, is selected from the group consisting of vegetable oils, free acids derived from these oils and $C_1$ to $C_6$ alkyl esters of these free acids.

14. The process as claimed in claim 13, wherein the vegetable oil is selected from sunflower oil, rape seed oil, soy bean oil, safflower oil, linseed oil and mixtures thereof.

* * * * *